US006487453B1

United States Patent
Kuzma et al.

(10) Patent No.: US 6,487,453 B1
(45) Date of Patent: Nov. 26, 2002

(54) ELECTRODE SYSTEM FOR OSSIFIED COCHLEA

(75) Inventors: Janusz A. Kuzma, Englewood, CO (US); Thomas H. R. Lenarz; Rolf-Dieter Battmer, both of Hannover (DE)

(73) Assignee: Advanced Bionics Corporation, Sylmar, CA (US)

( * ) Notice: Subject to any disclaimer, the term of this patent is extended or adjusted under 35 U.S.C. 154(b) by 97 days.

(21) Appl. No.: 09/585,848

(22) Filed: Jun. 1, 2000

Related U.S. Application Data
(60) Provisional application No. 60/148,135, filed on Aug. 9, 1999.

(51) Int. Cl.[7] ............................................. A61N 1/05
(52) U.S. Cl. ............................................................... 607/137
(58) Field of Search ................................. 600/379, 393; 607/55, 56, 57, 137

(56) References Cited

U.S. PATENT DOCUMENTS

| | | | |
|---|---|---|---|
| 4,809,712 A | 3/1989 | Kuzma .......................... 128/784 |
| 4,819,647 A | 4/1989 | Byers et al. .................... 128/642 |
| 5,344,387 A | 9/1994 | Lupin ............................ 600/25 |
| 5,545,219 A | 8/1996 | Kuzma .......................... 623/10 |
| 5,571,148 A | 11/1996 | Loeb et al. ..................... 607/57 |
| 5,578,084 A | 11/1996 | Kuzma et al. .................. 623/10 |
| 5,601,617 A | 2/1997 | Loeb et al. ..................... 607/57 |
| 5,603,726 A | 2/1997 | Schulman et al. .............. 607/57 |
| 5,645,585 A | 7/1997 | Kuzma .......................... 623/10 |
| 5,653,742 A | 8/1997 | Parker et al. ................... 607/137 |
| 5,755,747 A | 5/1998 | Daly et al. ..................... 607/55 |
| 5,800,500 A | 9/1998 | Spelman et al. ................ 607/137 |
| 5,833,714 A | 11/1998 | Loeb ............................. 607/56 |
| 5,876,443 A | 3/1999 | Hochmair et al. .............. 623/10 |
| 5,922,017 A * | 7/1999 | Bredberg et al. .............. 607/137 |
| 5,999,859 A | 12/1999 | Jolly ............................. 607/137 |
| 6,067,474 A | 5/2000 | Schulman et al. .............. 607/57 |
| 6,070,105 A | 5/2000 | Kuzma .......................... 607/137 |
| 6,078,841 A | 6/2000 | Kuzma .......................... 607/137 |
| 6,306,168 B1 * | 10/2001 | Berrang et al. ................. 623/10 |
| 6,321,125 B1 * | 11/2001 | Kuzma .......................... 607/137 |

FOREIGN PATENT DOCUMENTS

| WO | 9306698 | 4/1993 |
|---|---|---|
| WO | 9631807 | 10/1996 |
| WO | 0045618 | 8/2000 |

* cited by examiner

*Primary Examiner*—Jeffrey R. Jastrzab
*Assistant Examiner*—Frances P. Oropeza
(74) *Attorney, Agent, or Firm*—Bryant R. Gold

(57) ABSTRACT

An electrode system is provided for insertion into an ossified cochlea. The electrode system includes a first electrode array and a second electrode array, both of which are electrically connected to a suitable implantable cochlear stimulator (ICS). Each of the two electrode arrays has a plurality of spaced-apart electrode contacts along one side or surface thereof, e.g., eight to twelve electrode contacts on the first electrode array, and six to ten electrode contacts on the second electrode array. A tunnel is drilled through the ossified portion of the cochlea into which the first electrode array is snugly inserted. The second electrode array is inserted into the cochlea near the second turn thereof. Where the cochlea is fully ossified, a second tunnel is drilled through the ossified portion at the second turn. A positioner may be used with the second electrode array in order to position its electrode contacts against the modiolar wall of the cochlea. The first and second electrodes may be inserted into the scala tympani and/or the scala vestibuli of the cochlea.

9 Claims, 4 Drawing Sheets

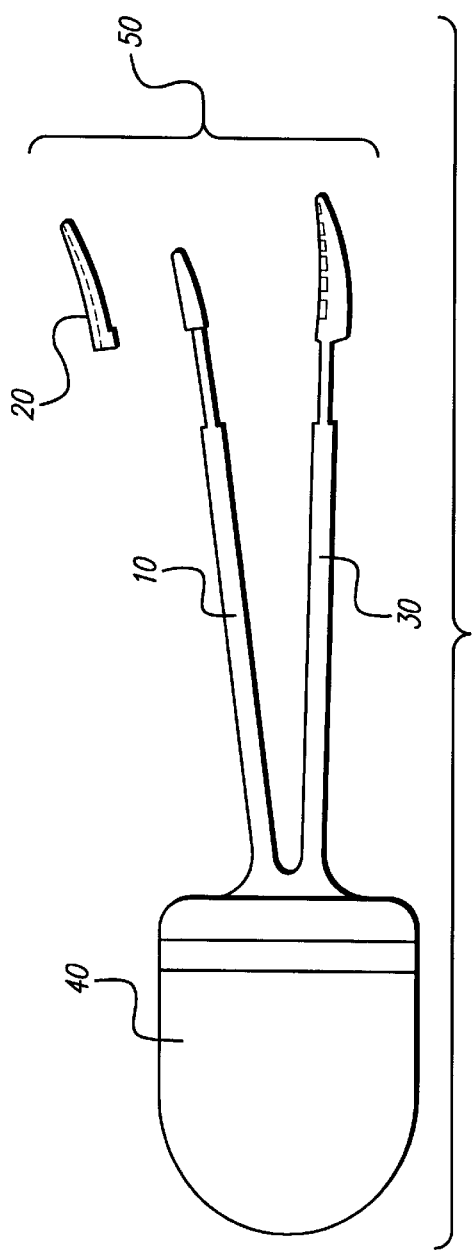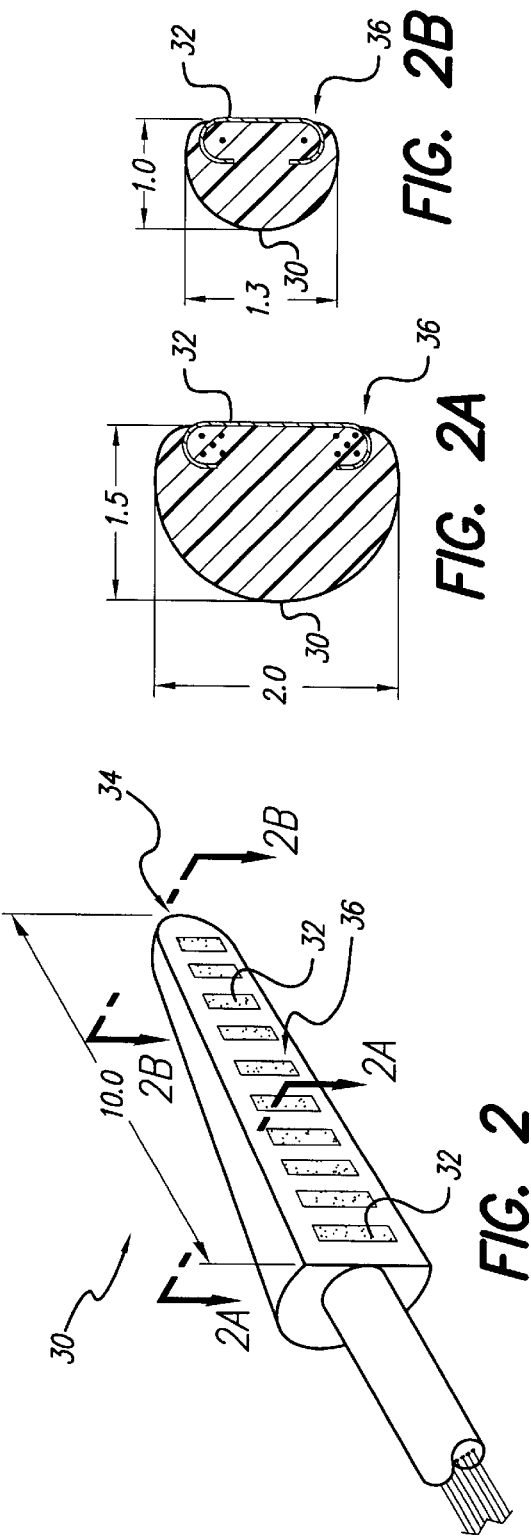

ELECTRODE SYSTEM FOR OSSIFIED COCHLEA

This application claims the benefit of United States Provisional Patent Application Serial No. 60/148,135, filed Aug. 9, 1999, which provisional patent application is incorporated herein by reference.

BACKGROUND OF THE INVENTION

The present invention relates to implantable stimulation devices, e.g., cochlear prosthesis used to electrically stimulate the auditory nerve, and more particularly to an electrode array for use within an ossified cochlea in conjunction with a cochlear stimulation system.

Hearing loss, which may be due to many different causes, is igenerally of two types: conductive and sensorineural. Of these, conductive hearing loss occurs where the normal mechanical pathways for sound to reach the hair cells in the cochlea are impeded, for example, by damage to the ossicles. Conductive hearing loss may often be helped by use of conventional hearing aids, which amplify sound so that acoustic information does reach the cochlea and the hair cells. Some types of conductive hearing loss are also amenable to alleviation by surgical procedures.

In many people who are profoundly deaf, however, the reason for their deafness is sensorineural hearing loss. This type of hearing loss is due to the absence or the destruction of the hair cells in the cochlea which are needed to transduce acoustic signals into auditory nerve impulses. These people are unable to derive any benefit from conventional. hearing aid systems, no matter how loud the acoustic stimulus is made, because their mechanisms for transducing sound energy into auditory nerve impulses have been damaged. Thus, in the absence of properly functioning hair cells, there is no way auditory nerve impulses can be generated directly from sounds.

To overcome sensorineural deafness, there have been developed numerous cochlear implant systems—or cochlear prosthesis—which seek to bypass the hair cells in the cochlear (the hair cells are located in the vicinity of the radially outer wall of the cochlea) by presenting electrical stimulation to the auditory nerve fibers directly, leading to the perception of sound in the brain and an at least partial restoration of hearing function. The common denominator in most of these cochlear prosthesis systems has been the implantation into the cochlea of electrodes which are responsive to suitable external source of electrical stimuli and which are intended to transmit those stimuli to the ganglion cells and thereby to the auditory nerve fibers.

A cochlear prosthesis operates by direct electrical stimulation of the auditory nerve cells, bypassing the defective cochlear hair cells that normally transduce acoustic energy into electrical activity in such nerve cells. In addition to stimulating the nerve cells, the electronic circuitry and the electrode array of the cochlear prosthesis performs the function of the separating the acoustic signal into a number of parallel channels of information, each representing the intensity of a narrow band of frequencies within the acoustic spectrum. Ideally, each channel of information would be conveyed selectively to the subset of auditory nerve cells that normally transmitted information about that frequency band to the brain. Those nerve cells are arranged in an orderly tonotopic sequence, from high frequencies at the basal end of the cochlear spiral to progressively lower frequencies towards the apex. In practice, this goal tends to be difficult to realize because of the anatomy of the cochlea.

Over the past several years, a consensus has generally emerged that the scala tympani, one of the three parallel ducts that, in parallel, make up the spiral-shaped cochlea, provides the best location for implantation of an electrode array used with a cochlear prosthesis. The electrode array to be implanted in this site typically consists of a thin, elongated, flexible carrier containing several longitudinally disposed and separately connected stimulating electrode contacts, perhaps 6–30 in number. In a non-ossified cochlea, such electrode array is pushed into the scala tympani duct to a depth of about 20–30 mm via a surgical opening made in the round window at the basal end of the duct.

Ossification is the formation of bone tissue. An ossified cochlea is thus a cochlea wherein the scala tympani duct, and/or other ducts within the cochlea, are filled completely or partially with bone growth tissue. Needless to say, it is not possible to insert an electrode into an ossified cochlea using conventional insertion techniques because the bone growth tissue blocks such insertion. Thus, there is a need for an effective cochlear electrode system which can be used for patients with ossification, whether such ossification only extends to the first turn of the scala tympani duct (partial ossified cochlea) or whether the ossification fills the entire scala tympani duct (fully ossified cochlea).

SUMMARY OF THE INVENTION

The present invention addresses the above and other needs by providing an electrode system for insertion into an ossified cochlea. Heretofore, there have been no electrode systems of which applicants are aware that have satisfactorily been useable with an ossified cochlea. Thus, heretofore, those patients having an ossified cochlea have not been able to benefit from implantation of a cochlear prosthesis.

The electrode system of the present invention includes a first electrode array and a second electrode array, both of which are electrically connected to a suitable implantable cochlear stimulator (ICS). Each of the two electrode arrays has a plurality of spaced-apart electrode contacts thereon, e.g., eight to twelve electrode contacts on the first electrode array, and six to eight electrode contacts on the second electrode array.

Where the cochlea is partially ossified, e.g., only up through the first turn of the scala tympani duct, a straight tunnel is drilled through the bone formation in the ossified scala tympani. This tunnel typically has a diameter of approximately 2 mm and a length of about 8–10 mm. The first electrode array is then inserted into this straight tunnel. The second electrode array is then placed through an additional cochleostomy drilled at the beginning of the second turn of the cochlea. An electrode positioner of the type disclosed in applicant Kuzma's copending patent application, Ser. No. 09/140,034, filed Aug. 26, 1998, incorporated herein by reference, may be used with this second electrode in order to assure that the second electrode hugs the modiolus of the cochlea as much as possible.

Where the cochlea is completely ossified, e.g., ossified through the second turn of the cochlea, a second tunnel is drilled through the ossification at the second turn of the cochlea, and the second electrode is inserted into this second tunnel. As needed, an electrode positioner may be inserted with the second-electrode in order to assure that the second electrode hugs the modiolus of the electrode.

For some patients, depending upon the degree of ossification, it may be desirable to insert the one or the two electrodes into a tunnel drilled in the ossified scala tympani, as described above, and to insert the other of the two electrodes into the scala vestibule.

It is thus an object of the present invention to provide an electrode system that may be used within an ossified cochlea.

It is an additional object of the invention to provide such an electrode system that, when used with a cochlear stimulation system, affords a patient having an ossified cochlea the opportunity to hear—an opportunity which heretofore has not been possible.

BRIEF DESCRIPTION OF THE DRAWINGS

The above and other features and advantages of the present invention will be more apparent from the following more particular description thereof, presented in conjunction with the following drawings wherein:

FIG. 1 diagrammatically illustrates an implantable cochlear stimulator (ICS) having a dual electrode array attached thereto in accordance with the teachings of the present invention;

FIG. 2 illustrates a perspective view of the first electrode array of the dual electrode array of FIG. 1, showing the spaced-apart electrode contacts that reside along one side of the first array;

FIG. 2A is a sectional view taken along the lines A—A of FIG. 2;

FIG. 2B is a sectional view taken along the lines B—B of FIG. 2, thereby showing, in comparison with FIG. 2A, a preferred tapering of the first electrode array;

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

The invention described herein teaches one type of electrode system 50 (FIG. 1) that may be used within an ossified cochlea. Such electrode 9 system is intended for use with a cochlear stimulation system 40, i.e., a cochlear stimulation system of the type disclosed in U.S. Pat. Nos. 5,603,726; and/or 5,601,617; and/or 6,067,474, all of which patents are incorporated herein by reference, or equivalents thereof.

Advantageously, the present invention may be used with just about any type of cochlear stimulation system that uses a cochlear electrode insertable into the cochlea. The details of how the cochlear stimulation system functions or operates are generally known in the art, and are not particularly relevant to the present invention.

Figure 3:
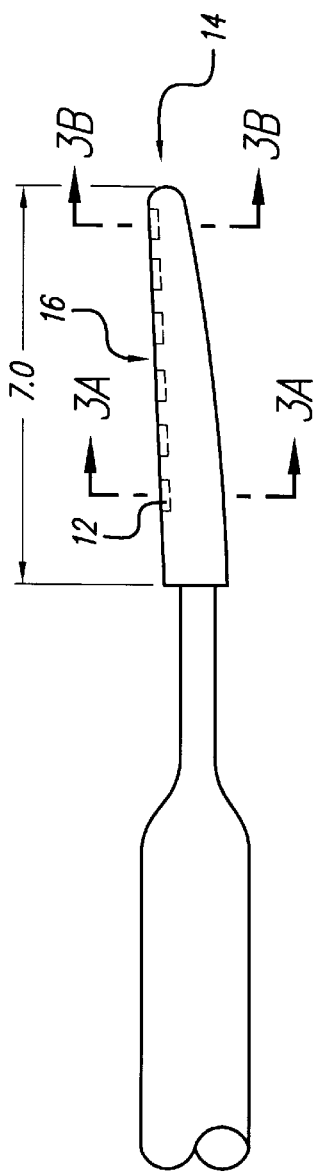
FIG. 3 diagrammatically illustrates the second electrode array of the dual electrode array of FIG. 1, showing the spaced-apart electrode contacts along one side of the second array.
Figure 3C:
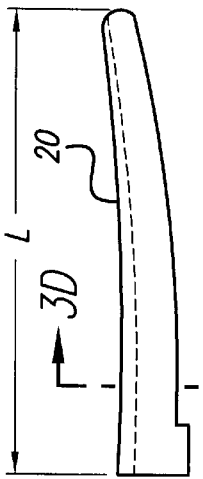
FIG. 3C is a side view of an electrode positioner that may be used with the second electrode array of FIG. 3.
Figure 3D:
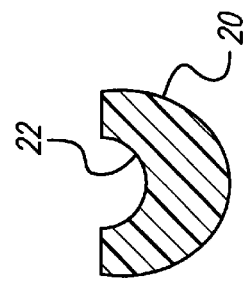
FIG. 3D is a sectional view taken along the lines D—D of FIG. 3C.
Figure 3B:
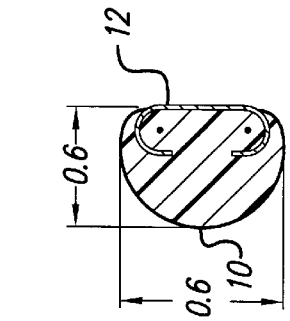
FIG. 3B is a sectional view taken along the lines B—B of FIG. 3, thereby showing, in comparison with FIG. 3A, a preferred tapering of the second electrode array.
Figure 3A:
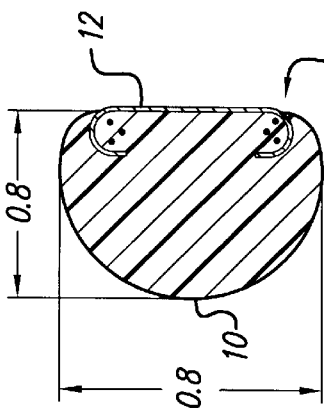
FIG. 3A is a sectional view taken along the lines A—A of FIG. 3.

As seen in FIG. 1, the implantable cochlear stimulator (ICS) 40 is connected to an electrode system 50. The electrode system 50 includes a first electrode 30, a second electrode 10, and an electrode positioner 20. Each of the electrodes 10 and 30 have an array of spaced-apart electrode contacts 12, 32 thereon through which electrical stimuli, generated by the ICS 40, may be applied to the cochlea, as is known in the art. The electrode 30 is best seen in FIGS. 2, 2A and 2B. The electrode 10 is best seen in FIGS. 3, 3A, and 3B. The total number of electrode contacts that may be stimulated by the ICS 40 is divided between the electrode contacts 32 of the electrode 30 and the electrode contacts 12 of the electrode 10. In one preferred embodiment, the electrode 30 has at least 10 electrode contacts 32, and the electrode 10 has at least 6 electrode contacts 12. It is to be emphasized, however, that these numbers of electrode contacts are intended to be only exemplary, and not limiting.

The electrode 30 is designed for insertion into the base of the scala tympani of the cochlea up to the first turn of the cochlea. For some patients, the electrode 30 may be instead inserted into the base of the scala vestibuli of the cochlea. As seen in FIG. 2, the electrode 30 typically has a length of about 10 mm. The width of the distal portion of the electrode 30—that part which actually is designed to be inserted into the cochlea—varies from about 1.3 mm diameter at the distal tip 34, to about 2.0 mm diameter at that point where the electrode contacts 32 begin (a distance of about 10 mm from the distal tip).

The electrode 10 (FIGS. 3, 3A and 3B) is designed for insertion into the second turn of the cochlea, as shown below in FIG. 5. Again, it is noted that for some patients, the electrode 10 may be instead inserted into the scala vestibuli of the cochlea. As seen in FIG. 3, the electrode 10 typically has a length of about 7 mm. The width of the distal portion of the electrode 10 varies from about 0.6 mm diameter at the distal tip 14, to about 0.8 mm diameter at that point where the electrode contacts 12 begin (a distance of about 7 mm from the distal tip 14).

In one embodiment, one side 36 of the electrode 30 may be flattened, and carries the electrode contacts 32, all of which face in the same direction. When inserted into the cochlea, this flattened side 36 faces the modiolar wall of the cochlea, closest to the spiral ganglion cells that are the intended targets of the stimulation provided through the electrode contacts. In a similar manner, one side 16 of the electrode 10 may be flattened, and this side 16 is the side on which all of the electrode contacts 12 are located. This flattened side 16 faces the modiolar wall of the cochlea when the electrode 10 is inserted into the second turn of the cochlea, as explained below.

The electrode 30, and the electrode 10, may be fabricated using any suitable manufacturing technique. The preferred manufacturing technique is the technique disclosed in U.S. patent application Ser. No. 09/140,034, filed Aug. 26, 1998, assigned to the same assignee as the present application, incorporated herein by reference.

Figure 4:
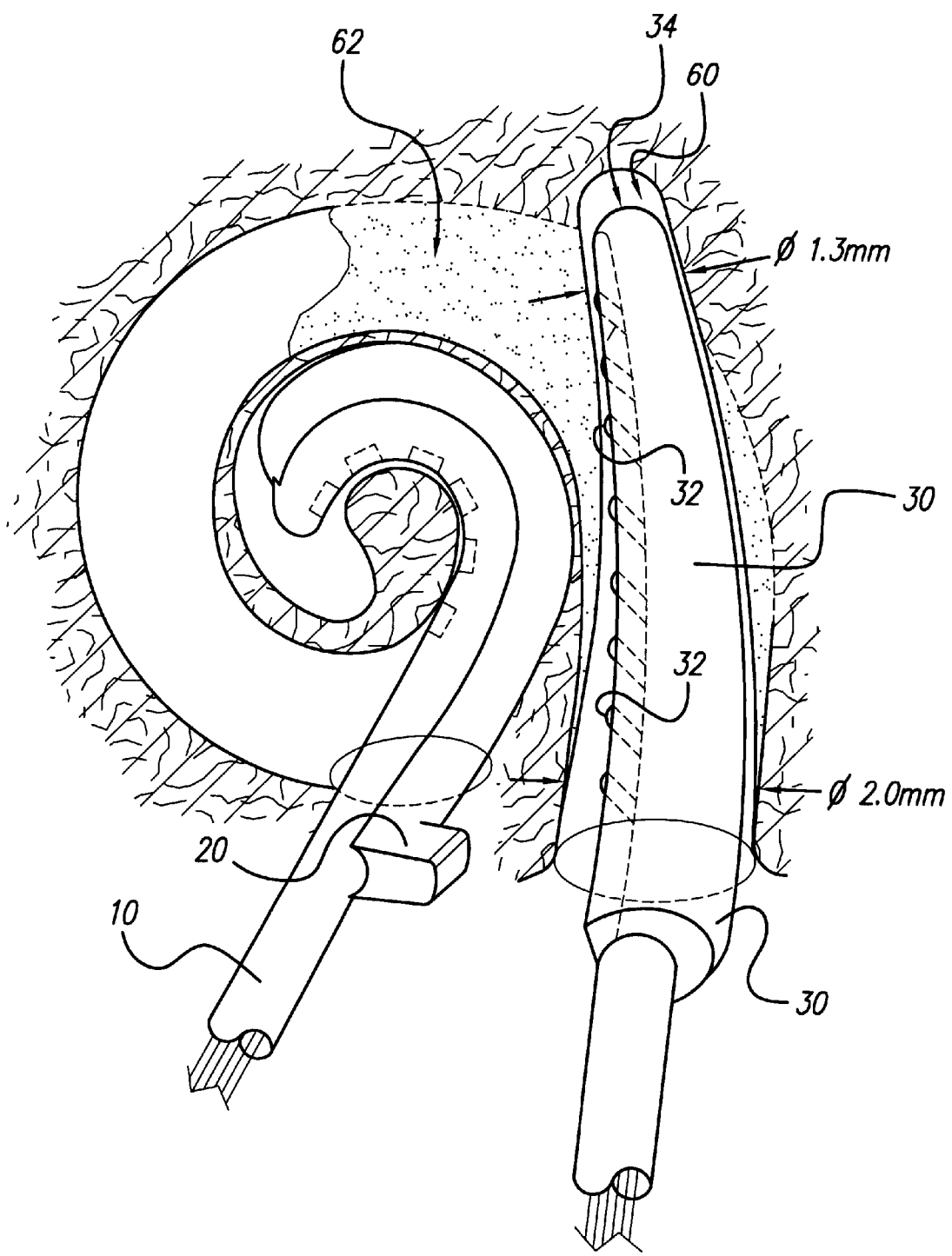
FIG. 4 illustrates the insertion of the dual electrode array of FIG. 1 into a partially ossified cochlea in accordance with the present invention.

The different lengths of the two electrodes 10 and 30 are determined by the size of the cochlea and the size of the tunnel(s) that may need to be drilled through the ossified portion of the cochlea. For a partially ossified cochlea, as seen in FIG. 4, a first straight tunnel 60, having a 2 mm diameter and a length of from 8–10 mm, is drilled through the ossified portion 62 of the cochlea, up to the first turn of the cochlea. The electrode 30 is then inserted into the tunnel 60 with the electrode contacts 32 facing inward towards the modiolar wall of the cochlea.

Figure 5:
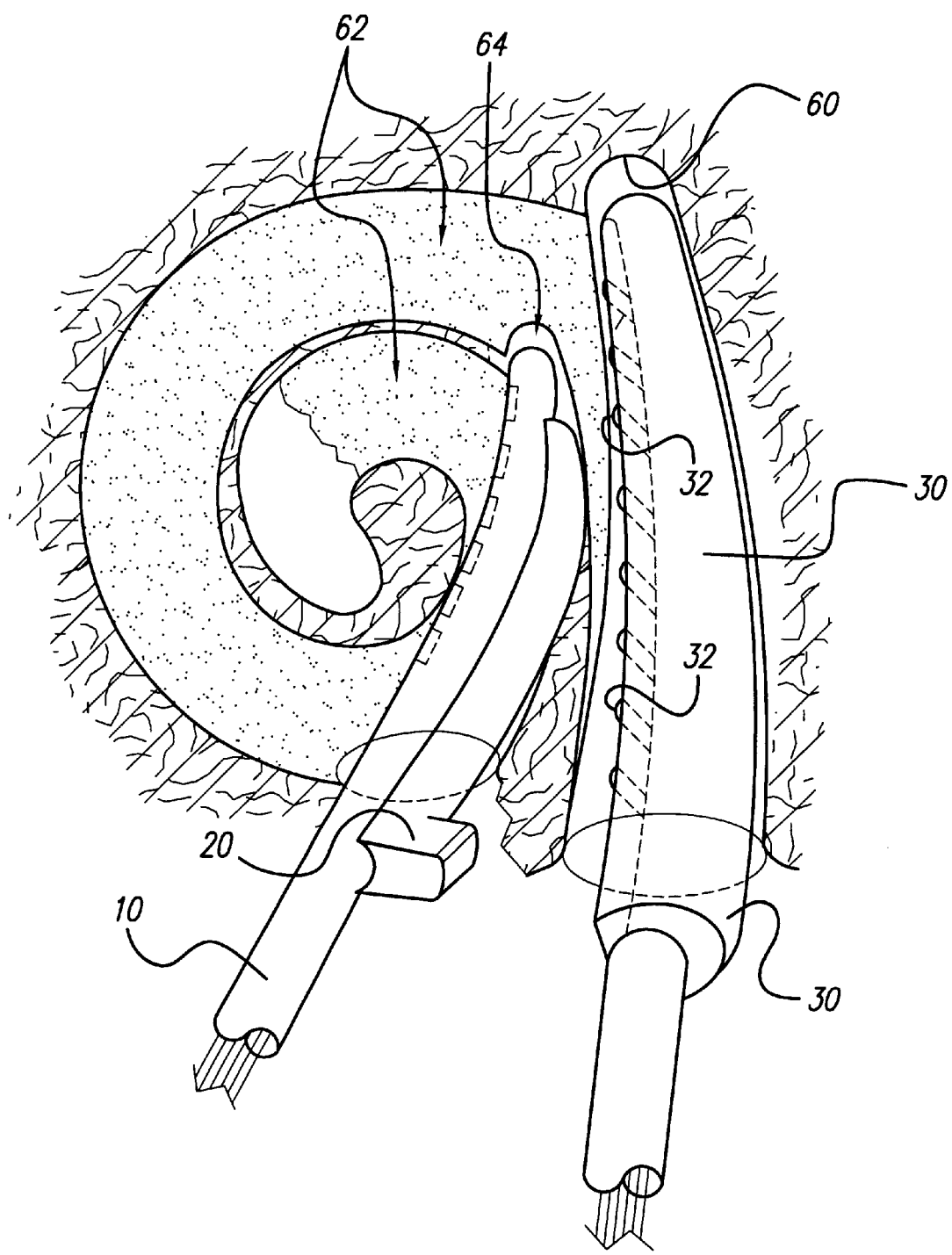
FIG. 5 shows the insertion of the dual electrode array of FIG. 1 into a fully ossified cochlea.

For a fully ossified cochlea, as seen in FIG. 5, a second tunnel 64, having a diameter of about 2 mm and a length of 6–7 mm, is drilled at the beginning of the second turn of the cochlea. The electrode 10 is inserted into the second tunnel 64 with the electrode contacts 12 all facing inward towards the modiolar wall. In order to place the electrode contacts 12 as close to the modiolar wall as possible, a positioner 20 may be slid behind the electrode 10 so as to fill the remaining space within the tunnel 64. Advantageously, the positioner 20 may include a groove 22 along one edge thereof. This groove 22 is intended to receive a back side of the electrode 10 when the positioner 20 is placed behind the electrode 10 within the tunnel 64.

The manufacture and use of a suitable positioner 20 is fully disclosed in the following commonly-owned United States Patent Applications, each of which is incorporated herein by reference: Ser. No. 09/216,063, filed Dec. 18, 1998; and Ser. No. 09/313,901, filed May 18, 1999.

Thus, as seen in FIGS. 2, 2A, 2B, 4 and 5, electrode 30 is placed in the drilled tunnel 62 of the ossified section of the scala tympani ro scala vestibule. The array of the electrode 30 has a length of about 10 mm, and a profile which provides a snug fit inside the tunnel 62 to maintain close and stable positioning of the electrode contacts 32 against the modiolar wall where the spiral ganglion cells are located. The construction and preferred dimensions of the electrode 30 are shown in FIGS. 2, 2A and 2B.

The large electrode contacts 32, placed on flat side 36 of the electrode 30, are preferably rectangular in shape having a width of about 0.3 mm and a length of about 0.8 mm. The technique for making this electrode is described in the previously referenced patent applications. The number of electrode contacts 32 is determined by the number of available stimulator outputs from the ICS 40. Where the ICS 40 includes 16 outputs, a preferred number of electrode contacts on the electrode 30 is ten, spaced about 0.9 mm apart.

As seen in FIGS. 3, 3A, 3B and 4 and 5, electrode 10 is placed either in the non-ossified portion of the scala tympani duct (FIG. 4) or in the drilled tunnel 64 of the ossified section of the scala tympani (FIG. 5). Alternatively, for some patients, it may be advantageous to place the electrode 10 in the scala vestibuli.

The length of the electrode 10 is about 7 mm with 6 electrode contacts 12 (when used with a sixteen output ICS 40). Other lengths and numbers of contacts may be employed, as dictated by the number of outputs available from the ICS 40. For example, if the ICS 40 has 24 outputs, then the electrode 30 could employ 12–18 electrode contacts, and the electrode 10 could employ 6–12 electrode contacts.

After insertion into the second turn of the cochlea, the electrode 10 is positioned against the modiolus through.the use of the positioner 20, as described above.

While the embodiment of the invention illustrated herein incorporates an electrode array construction having a flat surface on which the electrode contacts are located, the invention need not be limited to such electrode array configuration. That is, in some embodiments of the invention, it is contemplated that the first and second electrode arrays could have a generally oval or round cross-sectional shape, and the electrode contacts could be annular rings that encircle the cross-sectional shape, or segments of annual rings or other shapes that are exposed on only a portion of the surface of the array.

Thus, it is seen that the present invention provides an electrode system that may be used within an ossified cochlea. Advantageously, such invention affords a patient having an ossified cochlea the opportunity to hear with the aid of an implantable cochlear stimulator and electrode—an opportunity which heretofore has not been possible.

While the invention herein disclosed has been described by means of a specific embodiment and application thereof, numerous modifications and variations could be made thereto by those skilled in the art without departing from the scope of the invention set forth in the claims.

What is claimed is:

1. An electrode system for use within an ossified cochlea comprising:

a first flexible electrode array having a multiplicity of electrode contacts along a front surface thereof, wherein each of the electrode contacts of the first electrode array is electrically connected to a respective output channel of an implantable cochlear stimulator (ICS);

a second flexible electrode array having a multiplicity of electrode contacts along a front surface thereof, wherein each of the electrode contacts of the second electrode array is electrically connected to a respective output channel of the ICS which is not connected to the electrode contacts of the first electrode array; and a flexible positioner for use with the second flexible electrode array.

2. The electrode system as set forth in claim 1 wherein the front surface of each of the first and second electrode arrays is flat.

3. The electrode system as set forth in claim 2 wherein each of the electrode contacts of the first and second electrode arrays is rectangular in shape.

4. The electrode system as set forth in claim 2 further including means for drilling a relatively straight tunnel into ossified portions of the cochlea into which at least the first electrode array is inserted so that the flat front side of the first electrode array faces a modiolar wall of the ossified cochlea.

5. An electrode system for use within an ossified cochlea comprising:

a first flexible electrode array having a multiplicity of electrode contacts, wherein each of the electrode contacts of the first electrode array is electrically connected to a respective output channel of an implantable cochlear stimulator (ICS);

a second flexible electrode array having a multiplicity of electrode contacts, wherein each of the electrode contacts of the second electrode array is electrically connected to a respective output channel of the ICS which is not connected to the electrode contacts of the first electrode array; and an electrode positioner for insertion into the cochlea alongside one of the first or second flexible electrode arrays;

wherein the first flexible electrode array has a first side, and wherein the multiplicity of electrode contacts are all positioned on said first side.

6. The electrode system of claim 5 wherein the number of electrode contacts on the first side of the first flexible electrode array comprises at least 10 electrode contacts.

7. A method of stimulating spiral ganglion cells within an ossified cochlea comprising:

drilling a first tunnel into an ossified portion of the cochlea up to a first bend in the scala tympani or scala vestibuli of the cochlea;

inserting a first electrode array into the first tunnel, the first electrode array having a plurality of spaced-apart electrode contacts along one side thereof;

electrically connecting the electrode contacts of the first electrode array to a cochlear stimulator;

inserting a second electrode array into the cochlea near the location where the second turn of the cochlea begins, the second electrode array having a plurality of spaced-apart electrode contacts along only one side thereof inserting an electrode positioner into the cochlea alongside one of the first or second flexible electrode arrays;

electrically connecting the electrode contacts of the second electrode array to the cochlear stimulator; and controlling the cochlear stimulator so as to apply a pattern of stimulation pulses to the electrode contacts of the first and second electrode arrays.

8. The method of claim 7 further including positioning the electrode contacts of the first and second electrode arrays so that they face the modiolar wall of the cochlea when inserted into the cochlea.

9. The method of claim 7 further including drilling a second tunnel into ossified portions of the cochlea near the second bend of the cochlea, and inserting the second electrode array into the second tunnel.

* * * * *